(12) United States Patent
Wang et al.

(10) Patent No.: US 7,767,843 B2
(45) Date of Patent: Aug. 3, 2010

(54) PROCESS FOR THE PREPARATION OF PHENYLCARBAMATES

(75) Inventors: Zhi-Xian Wang, Brantford (CA); Stephen E. Horne, Burlington (CA); K. S. Keshava Murthy, Ancaster (CA)

(73) Assignee: Apotex Pharmachem Inc., Brantford (CA)

( * ) Notice: Subject to any disclaimer, the term of this patent is extended or adjusted under 35 U.S.C. 154(b) by 946 days.

(21) Appl. No.: 11/365,596

(22) Filed: Mar. 2, 2006

(65) Prior Publication Data

US 2007/0207990 A1 Sep. 6, 2007

(51) Int. Cl.
C07C 269/04 (2006.01)

(52) U.S. Cl. ..................................... 560/132
(58) Field of Classification Search ........................ None
See application file for complete search history.

(56) References Cited

U.S. PATENT DOCUMENTS

| 4,948,807 A | 8/1990 | Rosin et al. |
| 5,602,176 A | 2/1997 | Enz |
| 2007/0082989 A1* | 4/2007 | Glasgow et al. ............. 524/284 |

FOREIGN PATENT DOCUMENTS

| CA | 1284501 | | 5/1991 |
| CN | 1486973 | A | 4/2004 |
| EP | 0 193 926 | B1 | 9/1986 |
| GB | 2 409 453 | A | 6/2005 |
| WO | WO 03/101917 | A2 | 11/2003 |
| WO | WO 2004/037771 | A1 | 6/2004 |

OTHER PUBLICATIONS

Kreutzberger, Charles B. "Chloroformates and Carbonates." Kirk-Othmer Encyclopedia of Chemical Technology, vol. 6. Apr. 16, 2001.*
Carey, Francis A. "Solvent Effects." On-Line Learning Center for Organic Chemistry, Chapter 8. Mar. 15, 2003.*
Price, "Nucleophilic Substitution and Elimination," see section entitled "Nucleophilicity trends." URL:<http://www.lasalle.edu/~price/Nucleophilic%20Substitution.pdf> Accessed Nov. 10, 2009.*
Amstutz et al, Cyclische Phenyl-carbamate des Miotin-Typs und ihre Wirkung auf die Acetylcholinesterase, Helvetica Chimica Acta, 1990, pp. 739-753, vol. 73, Switzerland.
Boezio et al, Asymmetric, Catalytic Synthesis of -Chiral Amines Using a Novel Bis(phosphine) Monoxide Chiral Ligand, J. Am. Chem. Soc., 2003, 14260-14261, vol. 125, USA.
Journal of East China Normal University (Natural Science), 2001, 61-66.
Yong-Wen Jiang, et al., The Synthesis of Rivastigmine, A Chiral Drug for AD, Journal of East China Normal University (Natural Science), 2001, 61-66.

Ager, et al. "Handbook of Chiral Chemicals", (1999) pp. 222-225 Marcel Dekker, Inc. New York, USA.
Bhattacharyya, Suskanta, "Reductive Alkylations of Dimethylamine Using Titanium(IV) Isopropoxide and Sodium Borohydride: An Efficient, Safe, and Convenient Method for the Synthesis of N,N-Dimethylated Tertiary Amines", J. Org. Chem. (1995), 60, 4928-4929.
Bolognesi, Maria Laura, et al., "Design, Synthesis and Biological Evaluation of Conformationally Restricted Rivastigmine Analogues", J. Med. Chem., (2004), 47, 5945-5952.
Chen, Chung-Pin, et al., "A General Enantioselective Synthesis of alpha-Arylethylamines", Tetrahedron Letters, (1991) vol. 32, No. 49, pp. 7175-7178.
MacDonald, Joseph McL, et al., "The Resolution of alpha-m-Hydroxyphenylethyl-methylamine and the Prepartion of d- and l-Miotine (Methylurethanes of d- and l-alpha-m-Hydroxyphenyl-ethyldimethylamine).", Journal of the Chemical Society., (1932), Part II, pp. 2513-2519.
Mustazza, Carlo, et al., "Synthesis and cholinesterase activity of phenylcarbamates related to Rivastigmine, a therapeutic agent for Alzheimer's disease", Eur. J. Med. Chem., (2002), 37, 91-109.
Stedman, Edgar, et al., "The Methylurethanes of the Isomeric alpha-Hydroxyphenylethyldimethylamines and their Miotic Activity", Journal of the Chemical Society, (1929), Part I, pp. 609-617.
Toda, et al., "Design, Synthesis and Structure-Activity Relationships of Dual Inhibitors of Acetylcholinesterase and Serotonin Transporter as Potential Agents for Alzheimer's Disease", Bioorganic & Medicinal Chemistry, (2003), 11, 1935-1955.

* cited by examiner

*Primary Examiner*—Golam M. M. Shameem
*Assistant Examiner*—Alicia L Fierro

(57) ABSTRACT

A process for the preparation of aminoalkyl phenyl carbamate compounds of Formula I,

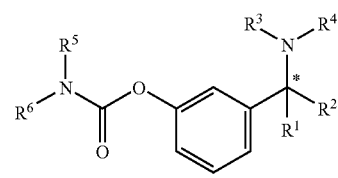

wherein $R^1$ and $R^2$ independently are hydrogen or a $C_{1-6}$ alkyl; $R^3$ and $R^4$ are the same or different and each is a $C_{1-6}$ alkyl; or $R^3$ and $R^4$ together with the nitrogen to which they are attached form a cyclic three to eight membered ring, with or without a heteroatom like nitrogen or oxygen; $R^5$ and $R^6$ independently are hydrogen, linear, branched or cyclic $C_{1-6}$ alkyl; or $R^5$ and $R^6$ together with the nitrogen to which they are attached form a cyclic three to eight membered ring, with or without a heteroatom like nitrogen or oxygen; the carbon centre designated "*" can be racemic or enantiomerically enriched in the (R)- or (S)- configuration; and pharmaceutically acceptable acid addition salts thereof.

26 Claims, No Drawings

PROCESS FOR THE PREPARATION OF PHENYLCARBAMATES

FIELD OF THE INVENTION

The present invention relates to a process for the preparation of aminoalkyl phenyl carbamates compounds of Formula I,

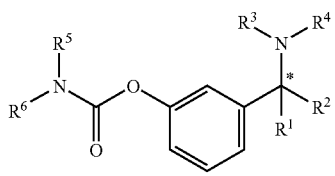

wherein $R^1$ and $R^2$ independently are hydrogen or a $C_{1-6}$ alkyl; $R^3$ and $R^4$ are the same or different and each is a $C_{1-6}$ alkyl; or $R^3$ and $R^4$ together with the nitrogen to which they are attached form a cyclic three to eight membered ring, with or without a heteroatom like nitrogen or oxygen; $R^5$ and $R^6$ independently are hydrogen, linear, branched or cyclic $C_{1-6}$ alkyl; or $R^5$ and $R^6$ together with the nitrogen to which they are attached form a cyclic three to eight membered ring, with or without a heteroatom like nitrogen or oxygen; the carbon center designated "*" can be racemic or enantiomerically enriched in the (R)- or (S)-configuration; and pharmaceutically acceptable acid addition salts thereof.

Particularly, the process of the present invention relates to the preparation of racemic and enantiomerically enriched forms of ethylmethylcarbamic acid 3-[1-(dimethylamino)ethyl]phenyl ester, commonly known as Rivastigmine.

BACKGROUND OF THE INVENTION

Certain aminoalkyl phenylcarbamates are selective acetylcholine esterase inhibitors and are therefore potentially useful as pharmaceuticals for the treatment of brain disorders such as dementia, Alzheimer's disease, Huntington's chorea, tardive dyskinesias, confusion disorders and ataxia. One such compound, the hydrogen tartrate salt of (S)-ethylmethylcarbamic acid 3-[1-(dimethylamino)ethyl]phenyl ester (Rivastigmine, 1), is marketed as a pharmaceutical for the treatment of dementia of the Alzheimer's type.

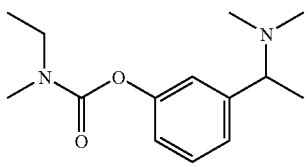

Rivastigmine, 1

Processes for the preparation of these types of aminoalkyl phenylcarbamates are described in patents U.S. Pat. No. 4,948,807, EP 193926, U.S. Pat. No. 5,602,176, GB 2409453, CN 1486973 and WO 04/037771. These patents disclose the preparation of phenyl carbamate compounds involving reaction of phenol compounds with appropriate isocyanates or carbamoyl halides. The process using isocyanates employs benzene as a solvent. Moreover, isocyanates such as lower alkyl isocyanates are hazardous to handle due to their toxic and volatile nature. Another reported alternative process uses carbamoyl halides along with reactive bases like sodium hydride, to prepare the carbamates. The carbamoyl halides are carcinogenic substances and are not easy to handle on an industrial scale. Moreover, the use of a reactive base like sodium hydride on an industrial scale is hazardous and operationally not user-friendly due to its pyrophoric and reactive nature.

PCT application WO 03/101917 discloses a process for the preparation of the title phenyl carbamate compounds involving reaction of phenol compounds with an alkylamine4-nitrophenyl carbamate. The process disclosed in WO 03/101917 partially overcomes the deficiency posed by the use of isocyanates or carbamoyl halides reported in the prior art. However, the reaction requires harsh conditions and long reaction times. For example, in Example 3 of WO 03/101917, the reaction of 3-(1-dimethylaminoethyl)phenol and N-ethyl-N-methyl-4-nitrophenyl carbamate was carried out in dimethylsulfoxide (DMSO) in the presence of anhydrous potassium carbonate at 90-100° C. for 35-40 hours. In addition, the reaction conditions may not be suitable because heating the chiral intermediate (S)-3-(1-dimethylaminoethyl)phenol with a base for an extended period of time may cause racemization of the chiral centre.

It is therefore an object of this invention to provide a more industrially applicable process for the preparation of aminoalkyl phenyl carbamate compounds.

It is a further object of the invention to use less toxic substances, such as for example 1,1'-carbonyldiimidazole, in the formation of racemic and enantiomerically-enriched (R)- or (S)-Rivastigmine, and their pharmaceutically acceptable addition salts.

Further and other objects of the invention will become apparent to those skilled in the art when considering the following summary of the invention and the more detailed description of the embodiments of the invention described herein.

SUMMARY AND DETAILED DESCRIPTION OF THE INVENTION

According to one aspect of the invention, a process is provided for the preparation of aminoalkyl phenyl carbamate compounds of Formula I,

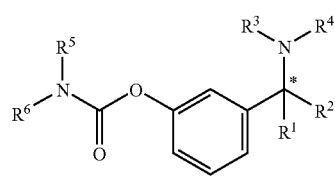

wherein $R^1$ and $R^2$ independently are hydrogen or a $C_{1-6}$ alkyl; $R^3$ and $R^4$ are the same or different and each is a $C_{1-6}$ alkyl; or $R^3$ and $R^4$ together with the nitrogen to which they are attached form a cyclic three to eight membered ring, with or without a heteroatom like nitrogen or oxygen; $R^5$ and $R^6$ independently are hydrogen, linear, branched or cyclic $C_{1-6}$ alkyl; or $R^5$ and $R^6$ together with the nitrogen to which they are attached form a cyclic three to eight membered ring, with or without a heteroatom like nitrogen or oxygen; the carbon centre designated "*" can be racemic or enantiomerically enriched in the (R)- or (S)-configuration; and pharmaceutically acceptable acid addition salts thereof comprising the steps of:

1) reacting in a solvent at a controlled temperature the compound of Formula II,

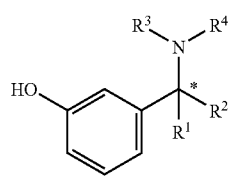

wherein $R^1$, $R^2$, $R^3$, $R^4$ and "*" are as defined above, with a carbonylating agent to form the compound of Formula III

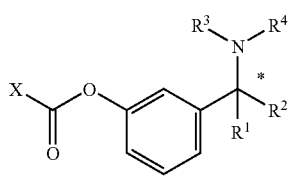

wherein $R^1$, $R^2$, $R^3$, $R^4$ and "*" are as defined above and X is a leaving group, followed by:

2) reacting in a solvent at a controlled reaction temperature the compound of Formula III with an amine $R^5R^6NH$, wherein $R^5$ and $R^6$ are as defined above, to form the compound of Formula I.

The aminoalkyl phenyl carbamates described herein form pharmaceutically acceptable acid salts with a wide variety of organic and inorganic acids.

Surprisingly, we have discovered that compounds of Formula III, when X is as described above, can react with an amine under mild conditions (i.e., mild reaction temperature, in the presence of water and short reaction time) to give compounds of Formula I in good yield and purity. The process avoids using carcinogenic substances such as carbamoyl halides and highly toxic reagents such as isocyanates. Furthermore, the stereochemical integrity of the chiral center is maintained. For this reason, this method is particularly useful for the preparation of enantiomerically-enriched aminoalkyl phenyl carbamates such as (S)-Rivastigmine.

The compounds of Formula II and the optically pure enantiomers can be obtained using the methods previously described in the art, for example, the methods disclosed in U.S. Pat. No. 4,948,807, EP 193926, CA 1,284,501, U.S. Pat. No. 5,602,176, WO 03/101917, WO 04/037771, CN 1486973, *Helv. Chim. Acta*, 1990, 73, 739-753, *Tetrahedron Lett.* 1991, 32, 7175-7178, *Handbook of Chiral Chemicals*, edited by David J. Ager, published by Marcel Dekker, Inc (1999), pp 222-223, *J. Amer. Chem. Soc.* 2003, 125, 14260-14261, and *Journal of East China Normal University (Natural Science)*, 2001, 61-65.

According to another aspect of the present invention, the leaving group X in compound III is selected from the group consisting of halogen such as chloro and bromo; substituted-phenoxyl groups such as 4-nitrophenoxyl, 4-chlorophenoxyl and 4-fluorophenoxyl; 1-haloalkoxyl groups such as 1-chloroethoxyl and 1,1,1-trichloromethoxyl; and imidazoles such as imidazolyl and N-methylimidazolyl. The preferable leaving groups are imidazolyl, 1,1,1-trichloromethoxyl, 1-chloroethoxyl, 4-nitrophenoxyl, 4-fluorophenoxyl and 4-chlorophenoxyl groups.

Compound III can be prepared from compound II using various carbonylating agents. For instance, treatment of compound II with a carbonylating agent such as phosgene, triphosgene, 1-chloroethyl chloroformate, 4-chlorophenyl chloroformate, 4-nitrophenyl chloroformate or 1,1'-carbonyldiimidazole provides compound III where X is chloro, 1,1,1-trichloromethoxy, 1-chloroethoxyl, 4-chlorophenoxyl, 4-nitrophenoxyl or imidazolyl, respectively. Compound III may be isolated from the reaction mixture and used for the next step, or it can be used directly without isolation. The one-pot approach is preferred because it employs less solvent, permits reduced process cycle times and furnishes improved yields.

The conversion of compound II to compound III is carried out in a solvent from about −50° C. to about 100° C., preferably from about −10° C. to about 50° C. Suitable solvents are selected from the group consisting of chlorinated hydrocarbons such as dichloromethane, dichloroethane and chlorobenzene; alkyl and aryl nitriles such as acetonitrile; alkyl carboxylic acid esters such as ethyl acetate and methyl acetate; cyclic or acyclic ethers such as 1,2-dimethoxyethane, dimethoxymethane, tetrahydrofuran and 1,4-dioxane; alkyl cyclic and acyclic amides such as N,N-dimethylformamide, N,N-dimethylacetamide and 1-methyl-2-pyrrolidinone; cyclic or acyclic alkyl sulfoxides and sulfones such as dimethylsulfoxide and tetramethylene sulfone; and aromatics such as toluene and xylenes. The preferred solvents are dichloromethane, acetonitrile, tetrahydrofuran, ethyl acetate and methyl acetate.

The reaction of compound III with the amine may be carried out in the same solvent as the previous step, or a different solvent selected from the group consisting of chlorinated hydrocarbons such as dichloromethane, dichloroethane and chlorobenzene; alkyl and aryl nitriles such as acetonitrile; alkyl carboxylic acid esters such as ethyl acetate and methyl acetate; cyclic or acyclic ethers such as 1,2-dimethoxyethane, dimethoxymethane, tetrahydrofuran and 1,4-dioxane; alkyl cyclic and acyclic amides such as N,N-dimethylformamide, N,N-dimethylacetamide and 1-methyl-2-pyrrolidinone; cyclic or acyclic alkyl sulfoxides and sulfones such as dimethylsulfoxide and tetramethylene sulfone; and aromatics such as toluene and xylenes. The preferred solvents are dichloromethane, acetonitrile, tetrahydrofuran, ethyl acetate and methyl acetate. The reaction temperature may range from about −10° C. to about 150° C., preferably from about 0° C. to about 70° C.

The amine $R^5R^6NH$ can be in its free base or acid addition salt form. Also, it can be used neat or as an aqueous solution.

The processes described above are capable of producing both enantiomerically enriched (R)- and (S)-stereoisomers and racemic mixtures of aminoalkyl phenyl carbamates of Formula I. It is understood by a person skilled in the art that the specific enantiomerically enriched stereoisomers may be obtained by resolving the racemic product, intermediates, or the starting materials. Thus, when a racemic mixture of aminoalkyl phenyl carbamates of Formula I are produced using the processes of the instant invention, the product can be resolved into its specific isomers, namely, the (R)- or (S)-stereoisomer.

The following non-limiting examples further illustrate the manner of carrying out the inventive process described herein.

EXAMPLE 1

A solution of 3-[1-(dimethylamino)ethyl]phenol (0.41 g, 2.5 mmoL) and triethylamine (0.8 g, 7.9 mmoL) in dichloromethane (10 mL) was stirred under nitrogen and cooled using an ice-bath. 1-Chloroethyl chloroformate (0.43 g, 3 mmoL) was added to the solution and the mixture was stirred for 1 h whereupon N-ethylmethylamine (0.24 g, 4 mmoL) was added and the solution was allowed to warm slowly to room temperature and stirred overnight. The reaction mixture was quenched by the addition of water (10 mL) and the pH of the aqueous layer was adjusted to >10 by the addition of aqueous NaOH solution. The organic layer was separated and the aqueous layer was extracted with additional dichloromethane. The combined organic extracts were washed with water and evaporated to dryness. The residue was dissolved in diethyl ether and extracted with dilute HCl solution. The pH of the aqueous solution was adjusted to >10 by the addition of aqueous NaOH solution and extracted with diethyl ether. The ethereal layers were washed with water and then evaporated to dryness to give racemic Rivastigime (0.5 g) as a liquid.

EXAMPLE 2

A solution of 3-[1-(dimethylamino)ethyl]phenol (0.41 g, 2.5 mmoL) and triethylamine (0.8 g, 7.9 mmoL) in dichloromethane (10 mL) was stirred under nitrogen and cooled using an ice-bath. 4-Nitrophenyl chloroformate (0.6 g, 3 mmoL) was added to the solution and the mixture was stirred for 1 h whereupon N-ethylmethylamine (0.24 g, 4 mmoL) was added and the solution was allowed to warm slowly to room temperature and stirred overnight. The reaction mixture was quenched by the addition of water (10 mL) and the pH of the aqueous layer was adjusted to >10 by the addition of aqueous NaOH solution. The organic layer was separated and the aqueous layer was extracted with additional dichloromethane. The combined extracts were washed with water and evaporated to dryness. The residue was dissolved in diethyl ether and extracted with dilute HCl solution. The pH of the aqueous solution was adjusted to >10 by the addition of aqueous NaOH and extracted with diethyl ether. The ethereal layers were washed with water and evaporated to dryness to give racemic Rivastigime (0.48 g) as a liquid.

EXAMPLE 3

A mixture of 3-[1-(dimethylamino)ethyl]phenol (0.82 g, 5 mmoL) in acetonitrile (5 mL) was stirred under nitrogen and cooled using an ice-bath. 1,1'-Carbonyldiimidazole (1.0 g, 6 mmoL) was added and the resulting solution was stirred at room temperature for 1.5 h. The solution was re-cooled using an ice-bath and acetic acid (1.0 g, 16.7 mmoL) was added followed by N-ethylmethylamine (0.5 g, 8.3 mmoL). The solution was allowed to warm slowly to room temperature and stirred for 3 hours. The reaction mixture was evaporated and the residue was dissolved in diethyl ether (20 mL). Water (10 mL) was added to the solution and the pH of the aqueous layer was adjusted to >10 by the addition of aqueous NaOH. The organic layer was separated and the aqueous layer was extracted with diethyl ether. The combined organic extracts were washed with water and evaporated to dryness to give racemic Rivastigime (0.8 g) as a liquid.

EXAMPLE 4

A mixture of 3-[1-(dimethylamino)ethyl]phenol (0.41 g, 2.5 mmoL) in acetonitrile (5 mL) was stirred under nitrogen at room temperature. 1,1'-Carbonyldiimidazole (0.5 g, 3.0 mmoL) was added to the mixture and the resulting solution was stirred at room temperature for 1.5 h. The solution was cooled using an ice-bath and acetic acid (0.5 g, 8.3 mmoL) was added followed by aqueous 40% N-ethylmethylamine solution (0.6 g, 4 mmoL). The solution was allowed to warm slowly to room temperature and stirred overnight. The reaction mixture was evaporated and the residue was dissolved in diethyl ether (15 mL). Water (10 mL) was added to the solution and the pH of the aqueous layer was adjusted to >10 by the addition of aqueous NaOH solution. The organic layer was separated and the aqueous layer was extracted with diethyl ether. The combined ethereal extracts were washed with water and evaporated to dryness to give racemic Rivastigime (0.38 g) as a liquid.

EXAMPLE 5

A mixture of 3-[1-(dimethylamino)ethyl]phenol (0.82 g, 5 mmoL) in acetonitrile (5 mL) was stirred under nitrogen and cooled using an ice-bath. 1,1'-Carbonyldiimidazole (1.1 g, 6.8 mmoL) was added and the resulting solution was stirred at room temperature for 2 h. The solution was re-cooled using an ice-bath and acetic acid (0.4 g, 8.3 mmoL) was added followed by N-ethylmethylamine hydrochloride (0.76 g, 10 mmoL) and triethylamine (1.0 g, 10 mmol). The solution was allowed to warm slowly to room temperature and stirred overnight. The reaction mixture was evaporated and the residue was dissolved in diethyl ether (20 mL). Water (10 mL) was added to the solution and the pH of the aqueous layer was adjusted to >10 by the addition of aqueous NaOH. The organic layer was separated and the aqueous layer was extracted with diethyl ether. The combined organic extracts were washed with water and evaporated to dryness to give racemic Rivastigime (0.6 g) as a liquid.

EXAMPLE 6

A mixture of (S)-3-[1-(dimethylamino)ethyl]phenol (1.64 g, 10 mmoL) in acetonitrile (10 mL) was stirred under nitrogen at 0-5° C. 1,1'-Carbonyldiimidazole (2.2 g, 13.5 mmoL) was added to the mixture and the resulting solution was stirred at room temperature overnight. The solution was cooled using an ice-bath and acetic acid (0.82 g, 13.5 mmoL) was added followed by N-ethylmethylamine (1.13g, 15 mmoL). The solution was allowed to warm slowly to room temperature and stirred overnight. The reaction mixture was evaporated and the residue was dissolved in diethyl ether (30 mL). Water (20 mL) was added to the solution and the pH of the aqueous layer was adjusted to >10 by the addition of aqueous NaOH solution. The organic layer was separated and the aqueous layer was extracted with diethyl ether. The combined ethereal extracts were washed with water and evaporated to dryness to give (S)-Rivastigime (1.8 g) as a liquid with enantiomeric purity >99.0% (chiral HPLC).

EXAMPLE 7

A solution of (S)-3-[1-(dimethylamino)ethyl]phenol (4.1 g, 25 mmoL) and triethylamine (8.0 g, 79 mmoL) in dichloromethane (40 mL) was stirred under nitrogen and cooled using an ice-bath. 4-Nitrophenyl chloroformate (6.0 g, 3 mmoL) was added to the solution and the mixture was stirred for 2 h whereupon N-ethylmethylamine (2.2 g, 37.5 mmoL) was added in portions and the solution was allowed to warm slowly to room temperature and stirred overnight. The reaction mixture was quenched by the addition of water (20 mL) and the pH of the aqueous layer was adjusted to >10 by the addition of aqueous NaOH solution. The organic layer was separated and the aqueous layer was extracted with additional dichloromethane. The combined extracts were washed with water and evaporated to dryness. The residue was dissolved in diethyl ether and extracted with dilute HCl solution. The pH of the aqueous solution was adjusted to >10 by the addition of aqueous NaOH and extracted with diethyl ether. The ethereal layers were washed with water and evaporated to dryness to give (S)-Rivastigime (4.2 g) as a liquid with enantiomeric purity >99.0% (chiral HPLC).

As many changes can be made to the invention without departing from the scope of the invention, it is intended that all material contained herein be interpreted as illustrative of the invention and not in a limiting sense.

The invention claimed is:

1. A process for the preparation of aminoalkyl phenyl carbamate compounds of Formula I,

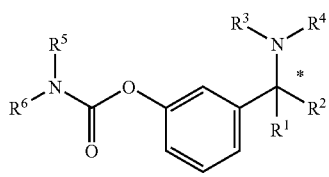

I wherein $R^1$ is hydrogen; $R^2$ is methyl; $R^3$ and $R^4$ are methyl; $R^5$ is methyl; $R^6$ is ethyl; and the carbon centre designated "*" is racemic, enantiomerically enriched in the (R)-configuration or enantiomerically enriched in the (S)- configuration; and pharmaceutically acceptable acid addition salts thereof comprising the steps of:

1) reacting in a solvent at a controlled reaction temperature the compound of Formula II,

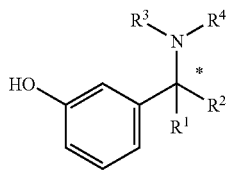

II wherein $R^1$, $R^2$, $R^3$, $R^4$ and "*" are as defined above, with a carbonylating agent to form the compound of Formula III

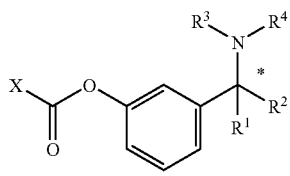

III wherein $R^1$, $R^2$, $R^3$, $R^4$ and "*" are as defined above and X is a leaving group, followed by:

2) reacting in a solvent at a controlled reaction temperature the compound of Formula III with an amine $R^5R^6NH$, wherein $R^5$ and $R^6$ are as defined above, to form the compound of Formula I.

2. The process according to claim 1 wherein the leaving group X is selected from the group consisting of halogens; phenoxyl groups; 1-chloroalkoxyl groups; and imidazoles.

3. The process according to claim 1 wherein the leaving group X is selected from the group consisting of imidazolyl, 1,1,1-trichloromethoxyl, 1-chloroethoxyl, 4-nitrophenoxyl, 4-fluorophenoxyl and 4-chlorophenoxyl groups.

4. The process according to claim 1 wherein the carbonylating agent is 1,1"-carbonyldiimidazole.

5. The process according to claim1 wherein the carbonylating agent is 1-chloroethyl chloroformate.

6. The process according to claim 1 wherein the carbonylating agent is 4-nitrophenyl chloroformate.

7. The process according to claim 1 wherein the carbonylating agent is 4-halophenyl chloroformate, wherein the halo is chloro or fluoro.

8. The process according to claim 1 wherein the carbonylating agent is triphosgene.

9. The process according to claim 1 wherein the solvent for the step 1) compound III formation is selected from the group consisting of chlorinated hydrocarbons; alkyl nitriles; aryl nitriles; alkyl carboxylic acid esters; cyclic ethers; acyclic ethers; alkyl cyclic amides; acyclic amides; cyclic alkyl sulfoxides; acyclic alkyl sulfoxides; cyclic alkyl sulfones; acyclic alkyl sulfones; and aromatics.

10. The process according to claim 9 wherein the solvent for the step 1) compound III formation is selected from the group consisting of dichloromethane, acetonitrile, tetrahydrofuran, ethyl acetate and methyl acetate.

11. The process according to claim 1 wherein the reaction temperature for the step 1) compound III formation ranges from −50° C. to 100° C.

12. The process according to claim 11 wherein the reaction temperature for the step 1) compound III formation ranges from −10° C. to 50° C.

13. The process according to claim 1 wherein the compound III is imidazole-1-carboxylic acid 3-[1-(dimethylamino)ethyl]phenyl ester.

14. The process according to claim 1 wherein the compound III is carbonic acid 1-chloroethyl 3-[1-(dimethylamino)ethyl]phenyl ester.

15. The process according to claim 1 wherein the compound III is carbonic acid 1,1,1-trichloromethyl 3-[1-(dimethylamino)ethyl]phenyl ester.

16. The process according to claim 1 wherein the compound III is carbonic acid 4-nitrophenyl 3-[1-(dimethylamino)ethyl]phenyl ester.

17. The process according to claim 1 wherein the compound III is carbonic acid 4-halophenyl 3-[1-(dimethylamino)ethyl]phenyl ester, wherein halo is chloro or fluoro.

18. The process according to claim 1 wherein the solvent used in the step 2) reaction of compound III and the amine is selected from the group consisting of chlorinated hydrocarbons; alkyl nitriles; aryl nitriles; alkyl carboxylic acid esters; cyclic ethers; acyclic ethers; alkyl cyclic amides; alkyl acyclic amides; cyclic alkyl sulfoxides; acyclic alkyl sulfoxides; cyclic alkyl sulfones; acyclic alkyl sulfones; and aromatics.

19. The process according to claim 18 wherein the solvent used in the step 2) reaction of compound III and the amine is selected from dichloromethane, acetonitrile, tetrahydrofuran, ethyl acetate or methyl acetate.

20. The process according to claim 1 wherein the reaction temperature for the step 2) reaction of compound III and the amine ranges from −10° C. to 150° C.

21. The process according to claim 20 wherein the reaction temperature for the step 2) reaction of compound III and the amine ranges from 0° C. to 70° C.

22. A process for the preparation of ethylmethylcarbamic acid 3-[1-(dimethylamino)ethyl]phenyl ester and its enantiomerically enriched (R)- or (S)-enantiomers comprising reacting 3-[1-(dimethylamino)ethyl]phenol with 1) 1-chloroethyl chloroformate and 2) N-ethylmethylamine, its aqueous solution or acid addition salt.

23. A process for the preparation of ethylmethylcarbamic acid 3-[1-(dimethylamino)ethyl]phenyl ester and its enantiomerically enriched (R)- or (S)-enantiomers comprising reacting 3-[1-(dimethylamino)ethyl]phenol with 1) 4-nitrophenyl chloroformate and 2) N-ethylmethylamine, its aqueous solution or acid addition salt.

24. A process for the preparation of ethylmethylcarbamic acid 3-[1-(dimethylamino)ethyl]phenyl ester and its enantiomerically enriched (R)- or (S)-enantiomers comprising reacting 3-[1-(dimethylamino)ethyl]phenol with 1) 4-halophenyl chloroformate, wherein the halo is chloro or fluoro, and 2) N-ethylmethylamine, its aqueous solution or acid addition salt.

25. A process for the preparation of ethylmethylcarbamic acid 3-[1-(dimethylamino)ethyl]phenyl ester and its enantiomerically enriched (R)- or (S)-enantiomers comprising reacting 3-[1-(dimethylamino)ethyl]phenol with 1) 1,1'-carbonyldiimidazole and 2) N-ethylmethylamine, its aqueous solution or acid addition salt.

26. A process for the preparation of ethylmethylcarbamic acid 3-[1-(dimethylamino)ethyl]phenyl ester and its enantiomerically enriched (R)- or (S)-enantiomers comprising reacting 3-[1-(dimethylamino)ethyl]phenol with 1) triphosgene and 2) N-ethylmethylamine, its aqueous solution or acid addition salt.

\* \* \* \* \*